United States Patent [19]

Slama

[11] Patent Number: 4,469,110

[45] Date of Patent: Sep. 4, 1984

[54] DEVICE FOR CAUSING A PINPRICK TO OBTAIN AND TO TEST A DROP OF BLOOD

[76] Inventor: Gérard J. Slama, 17, Av. du Château, 94210 La Varenne Saint Hilaire, France

[21] Appl. No.: 389,393

[22] Filed: Jun. 17, 1982

[30] Foreign Application Priority Data

Jun. 25, 1981 [FR] France .................. 81 12458

[51] Int. Cl.³ .............................. A61B 17/34
[52] U.S. Cl. .................. 128/770; 128/771; 128/637; 128/314
[58] Field of Search ............... 128/314–315, 128/329, 771, 743–744, 636–637, 760, 763, 765, 770

[56] References Cited

U.S. PATENT DOCUMENTS

| 55,620 | 6/1866 | Capewell | 128/314 |
|---|---|---|---|
| 2,235,436 | 3/1941 | Laub | 128/743 |
| 2,945,491 | 7/1960 | Gibbs | 128/636 |
| 3,030,959 | 4/1962 | Grunert | 128/329 |
| 3,086,530 | 4/1963 | Groom | 128/329 |
| 3,208,452 | 9/1965 | Stern | 128/329 X |
| 3,266,868 | 8/1966 | Harvill | 128/771 X |
| 3,419,000 | 12/1968 | Phillips | 128/771 X |
| 3,620,676 | 11/1971 | Davis | 128/771 X |
| 3,786,510 | 1/1974 | Hodges | 128/771 X |
| 3,800,780 | 4/1974 | Elliott | 128/771 X |
| 3,918,433 | 11/1975 | Fulsz | 128/771 X |
| 4,027,660 | 6/1977 | Wardlaw et al. | 128/771 |
| 4,203,446 | 5/1980 | Hofert et al. | 128/329 R |

Primary Examiner—Lee S. Cohen
Assistant Examiner—Angela D. Sykes
Attorney, Agent, or Firm—Lane, Aitken & Kananen

[57] ABSTRACT

For causing a pinprick on a user's skin to obtain a drop of blood, a movable holder which holds a pin, actuated by a spring, is tensioned.

In the normal, inactive position of the spring which is shown in the drawing, the pin is on this side of the edge of the end, and there exists a distance X between a radial shaft having a control button and a stop.

When the mechanism is triggered, the spring suddenly pushes the holder, and the shaft passes the normal position to reach the stop which limits its course in such a way that the pin projects, attaining a predetermined extreme position and returning automatically to its protected position.

4 Claims, 5 Drawing Figures

DEVICE FOR CAUSING A PINPRICK TO OBTAIN AND TO TEST A DROP OF BLOOD

BACKGROUND OF THE INVENTION

Patients with certain illnesses like diabetes, must verify several times a day the sugar content of their blood.

According to this content, the patient must or must not take certain medicines.

Since such tests have to be made frequently, it is indispensable that the patient has with him a portable device which he can easily and safely operate, because he may not be able to get help from a third person and is even less likely to find a laboratory which specializes in such tests.

For this reason, portable devices already exist, but they are not entirely satisfactory, particularly with respect to their size and easy handling.

For example, a device is known which comprises a body and a pin-carrying, movable holder which pivots relative to the body according to a movement which resembles that of a hammer in firearms and is acted upon by a spring toward its active position.

The holder is outside of the body, and since it carries the pin, the latter can accidentally injure the user even when the device is not in use, i.e. independently of any involuntary action on a control device which must be actuated to free the holder at the desired moment so that the pin is very lightly injected into the skin.

Devices are also known whose holder is inside a body but is attained by assembling half-shells of stiff synthetic material of parallelepipedal shape and is relatively bulky.

Moreover, their shape and dimensions make them unsuitable for thorough cleaning.

Also known is German Pat. No. 459.483 which describes a device of the same type as that of the present invention. However the stop m which limits the projection of the pin d outside the body a is formed by a screw nut which is more or less screwed onto a threaded shaft b in such a way that this screw nut, far from forming a foolproof fixes point, is during each use subjected to shocks against the upper portion e of the body a, thus risking an involuntary displacement which renders the coming out of the point d uncertain.

In such a structure there is no safe reference point on which the user can rely.

The user is therefore obliged to set the device by experience (and thus unreliably) each time it is to be used.

Another basic difference results from the fact that a large portion of the device is positioned outside of the body a, i.e. the threaded shaft b on its entire length, the screw nut m and a stopper without reference which is located at the end of the threaded shaft b.

This bulky device is even impractical in its design, because, since the extraction of the point d by means of the screw nut m is to be regulated, it is impossible to provide the latter inside the body a, as it would be inaccessible and invisible.

SUMMARY OF THE INVENTION

The present invention obviates these shortcomings because the projection of the point d is limited in a foolproof manner by a stop which determines the maximal possible projection.

It is an object of the invention to provide a device for causing a pinprick by means of a pin for the purpose of obtaining a drop of blood to be studied, especially by bringing it in contact with a reagent, said device being of the type comprising a body in which a movable pinholder is mounted and actuated by a spring between a withdrawn position inside said body and one of maximal projection outside said body, with said projection being determined by a stop with which the holder or a piece integral therewith cooperates to determine the maximal position of projection beyond the normal position which is determined by the length of a spring when not tensioned, characterized in that the stop is fixed, whereas the total length of the body is adjustable by means of a piece connected to the body, adjustable in position, but independent of the movable pieces.

According to other features of the invention:

the piece is formed of a sleeve, positioned at the end of the body where the aperture is located through which the pin is to project;

the piece carries a graduation scale which functions in connection with a mark on the body;

the body has in general the shape of a pen and comprises a cap, closed by a transverse partition to constitute a receptacle which is adapted to be closed by a stopper and is to contain strips of any type known per se and intended for receiving by capillary action the drop of blood which appears after pricking, with said receptacle being adapted to be provided at the inside by a humidity-absorbing product, such as a dessicating capsule.

BRIEF DESCRIPTION OF THE DRAWINGS

The invention will be better understood by referring to the following detailed description and drawings which are not limitative but serve only as examples.

DESCRIPTION OF THE PREFERRED EMBODIMENT

Figure 1:
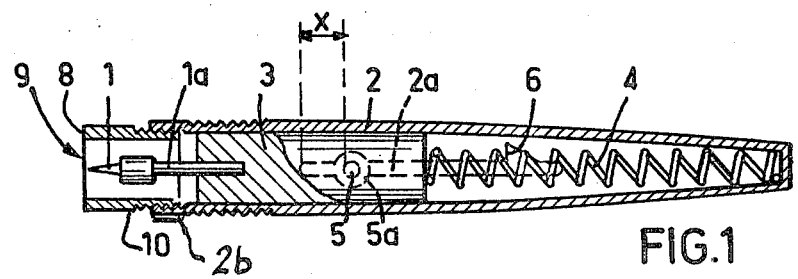
FIG. 1 is a schematic view in section of a device according to the invention, showing it in its normal position when the spring is not tensioned.

Referring now to the drawings, it can be seen that a device according to the invention comprises a pin 1 which is integral with a shaft 1a, by means of which it can be removably fastened to a movable holder 3 which is formed here by a cylinder mounted slidingly in the also cylindrical interior of a body 2 in the shape of a pen.

A spring 4 is placed in the body 2 and engages with one side the bottom of the body 2 and with the other side the holder 3 which is provided with a radial shaft 5, ending in a button 5a and which forms control means.

The shaft 5 is provided in an opening 2a of the body 2 which has a form, well known per se, where a first stop 6 and a second stop 7 are used.

The operation of the device is as follows: When the spring 4 is in its normal, inactive position, as shown in FIG. 1, its length is such that the pin 1 is positioned at the most on the level of the edge 8 of the opening 9 through which the pin will project from the body 2; and in the example shown in the figure the pin 1 is clearly on this side of the edge 8.

This means that the pin 1 is still protected when the device is not used and cannot accidentally injure the user. It can be seen that in this position (FIGS. 1 and 2) the shaft 5 is clearly positioned before the stop 7 since it is separated therefrom by a distance x.

Figure 3:
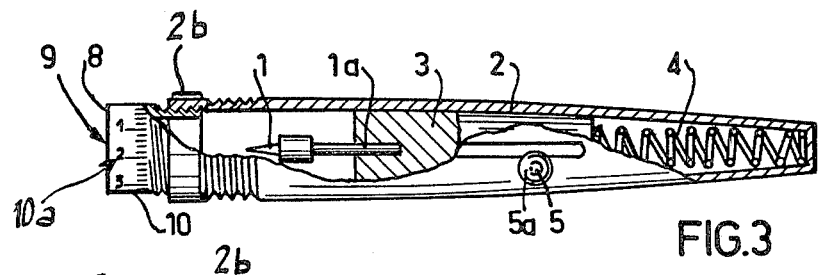
FIG. 3 is a schematic view, partially in section, with the spring being at maximum tension, i.e. when the holder is in loaded position.

For making the device ready so that it can be used, one actuates the button 5a to guide the shaft 5 opposite the stop 6, which is attained through compressing the spring 4 by sliding of the holder 3 in the body 2, with the shaft 5 moving freely in the opening 2a. When the button 5a arrives at the maximum of its course, the unit is lightly pivoted transversely around the general axis of the body 2 so that the shaft 5 is placed opposite the stop 6, which immobilizes the unit in this position (FIG. 3).

Next, the edge 8 of the opening 9 is placed against a location A of the human body (which is usually a finger), and the button 5 is pivoted in the reverse sense from before so that the shaft 5 leaves the stop 6 and goes back into the opening 2a. The movable holder is thus not held any more, and the spring 4 expands suddenly in such a way that it projects the holder 3, in that it goes beyond its normal position (FIGS. 1 and 2), which has the effect of causing the pin 1 to go beyond the edge 8 of the opening 9, thus penetrating into the skin A of the patient.

Figure 2:
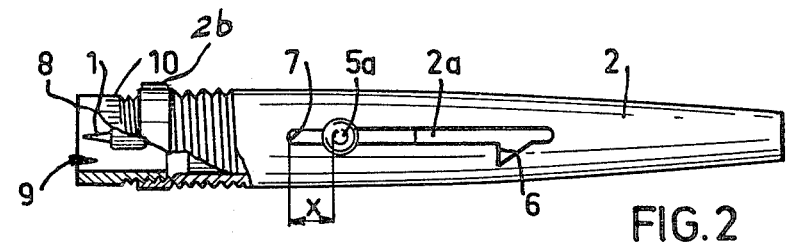
FIG. 2 is a schematic outside view, partially in section, of the same body with the same spring position.

The shaft 5 reaches finally the stop 7 which prevents a complete extraction of the movable holder 3 and/or of the pin 1 and which determines accurately the course of the pin 1 outside the device, i.e. its penetration into the skin of the patient. When the spring 4 exceeds its normal, inactive position, it returns to it by bringing the pin 1 back inside the body 2, in such a way that the unit regains its neutral position which is shown in FIGS. 1 and 2 and where the pin 1 is again covered. The end of the body 2 is made of a relatively stiff material, and it is necessary to have the pin 1 positioned sufficiently close to the edge 8, so that there is full assurance that upon a sudden release of the spring 4, the pin 1 is projected over a sufficiently long distance to prick the skin correctly.

According to one embodiment of the invention and as shown in the drawing, the end of the body 2 where the opening 8 is located through which the pin 1 is to project, is made of the threaded sleeve 10 whose advance relative to the body 2 can be set in this manner.

Due to this arrangement, the point of the pin 1 can penetrate more or less deeply into the skin according to the degree of screwing the sleeve 10 into the body.

Thereby the total length of the body 2 can be adjusted.

As a result of these arrangements each user can set the desired depth of penetration according to his skin and his preference.

For facilitating the adjustment, a graduation scale 10a has been provided on the sleeve 10 and a mark 2b on the body 2.

The stopping of the shaft 5 by the stop 7 determines its maximum course in such a way that the penetration can be regulated but remains constant for one and the same user.

The length of the sleeve 10 can be set in such a way that the pin 1 is easily accessible when the sleeve 10 is removed so that the pin 1 can either be replaced or can be easily and thoroughly cleaned. It is, of course, possible to cause a slow and controlled projecting of the pin 1 by actuating the button 5a toward the stop 7.

The typical form of a device according to the invention is that of a pen because this form does not only allow a good holding by the hand which operates the device, but also affords an excellent visibility of the exact location where the pricking of the skin is to take place, because no other portion of the body 2 exceeds the diameter of its end which can be relatively small and can be similar to the point of a mechanical pencil or a ballpoint pen.

According to the invention, the body 2 in form of a pen comprises a cap 11 which is closed by a transverse partition 12, serving as a receptacle which can be closed by a stopper 13.

Into the cap 11 a small supply of strips 14 of any type known per se has been placed and is intended to receive by capillary action the drop of blood appearing at the pricked spot.

The capillary capabilities of these strips have the consequence that they are particularly sensitive to humidity in such a way that according to the invention the cap 11 can be provided inside with a product absorbing humidity and, particularly, a dessication capsule 15.

The elongate and thin shape of the body 2 renders it especially suitable for holding a colorimetric scale 16 of any type known per se.

After a drop of blood has been picked up by a strip 14 and after the reagent with which the strip 14 is impregnated has taken effect, the user brings the strip 14 close to the colorimetric scale 16 to find out which colored part of the scale 16 comes closest to the strip 14 that was used, in order to determine the rate of the blood's sugar content.

The colorimetric scale 16 can, for example, be one which is normally placed into a new container of strips 14, in which case a small transparent housing is provided on the body 2, whereinto the colorimetric scale is inserted.

Said scale is thus constantly protected and is not subject to any use. It can also not get lost because the user puts back the cap 11 onto the body 2 after having used the device. It is, for example, put back by means of a screw thread as shown; and the unit can then be kept in a pocket like a regular pen by means of a clip 11a.

It should be understood that the described device can be modified, particularly with respect to the control mechanism because someone skilled in the art knows that many methods exist for causing the sudden release of a spring and the maintenance of its position under tension.

Figure 4:
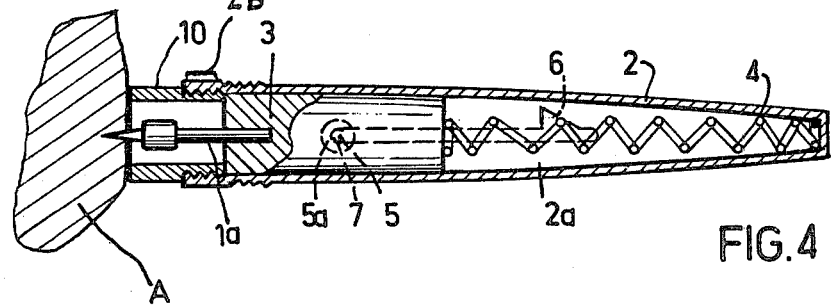
FIG. 4 is a schematic view, partially in section, showing the device in the position of use, during the brief moment of the sudden release of the spring which causes the projection of the pin beyond the end of the body.
Figure 5:
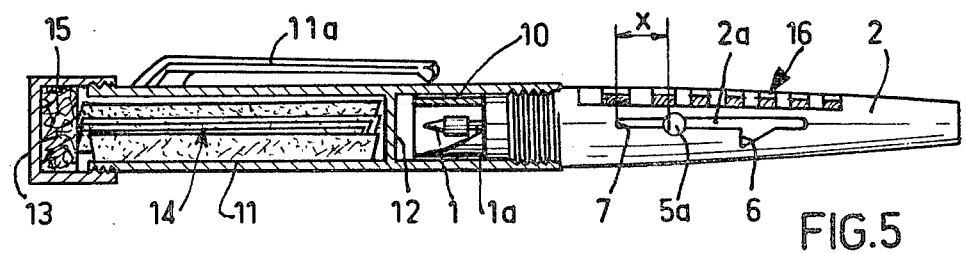
FIG. 5 is a schematic view in partial section showing the assembly of the body of the device with a cap containing a supply of strips.

The relative position of the pin 1 and the edge 8 of the body 2 (here sleeve 10) has three characteristic situations:
normal, inactive position; (FIGS. 1 and 2);
loaded position (FIG. 3);
flying position of use (FIG. 4).

Different means besides screw threads may be used for the purpose of fixing the sleeve 10 and the cap 11 on the body 2 or the stopper 13 on the cap 11, which are well known. The reason therefor is that the price of screw threads is relatively high, and the pieces could well be made by extraction of synthetic materials which is recommended here.

What is claimed is:

1. A device for causing a pin prick to obtain and test a drop of blood comprising an elongated body in the general shape of pen and having an open end, pricking means within said body for causing a pin prick from said open end of said body and drawing a drop of blood, a removable cap closing said open end of said body and a defining a receptacle within said cap, said receptacle having an opening therein and being adapted to retain therein a strip of the type for receiving by capillary action a drop of blood, a removable tip closing said receptacle and comprising a housing communicating with said receptacle adapted to receive and retain a desiccant material.

2. A device according to claim 1 wherein said body includes a housing containing a removable colorimetric scale.

3. A device according to claim 2 wherein said body housing is transparent.

4. A device as recited in claim 4, wherein a strip for receiving by capillary action a drop of blood is contained within said receptacle and a desiccant material is contained within the housing defined by said tip.

* * * * *